United States Patent
Didier et al.

(10) Patent No.: US 6,956,124 B2
(45) Date of Patent: Oct. 18, 2005

(54) PROCESS FOR THE PREPARATION OF 4, 10β-DIACETOXY-2α-BENZOYLOXY-5β,20-EPOXY-1,13α-DIHYDROXY-9-OXO-19-NORCYCLOPROPA[G]TAX-11-ENE

(75) Inventors: Eric Didier, Paris (FR); Guy Amouret, Fresnes (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/824,030

(22) Filed: Apr. 14, 2004

(65) Prior Publication Data

US 2004/0248969 A1 Dec. 9, 2004

Related U.S. Application Data

(60) Provisional application No. 60/482,598, filed on Jun. 26, 2003.

(30) Foreign Application Priority Data

Apr. 14, 2003 (FR) ............................................. 03 04613

(51) Int. Cl.⁷ .............................................. C07D 305/00
(52) U.S. Cl. ........................................ 549/510; 549/511
(58) Field of Search ................................. 549/510, 511

(56) References Cited

FOREIGN PATENT DOCUMENTS

| WO | WO 94/13654 | 6/1994 |
|----|-------------|--------|
| WO | WO 95/20582 | 8/1995 |
| WO | WO 95/33736 | 12/1995 |
| WO | WO 95/33737 | 12/1995 |
| WO | WO 96/13494 | 5/1996 |
| WO | WO 96/32387 | 10/1996 |

*Primary Examiner*—Amelia A. Owens
(74) *Attorney, Agent, or Firm*—Balaram Gupta

(57) ABSTRACT

There is disclosed a process for the preparation of 4-acetoxy-2α-benzoyloxy-5β,20-epoxy-1,13α-dihydroxy-9-oxo-19-norcyclopropa[g] tax-11-ene from 4-acetoxy-2α-benzoyloxy-5β,20-epoxy-1,13α-dihydroxy-9-oxo-7β-(trifluoromethyl sulfonyloxy) tax-11-ene by reaction with a molecular sieve in sulfolane.

20 Claims, No Drawings

PROCESS FOR THE PREPARATION OF 4, 10β-DIACETOXY-2α-BENZOYLOXY-5β,20-EPOXY-1,13α-DIHYDROXY-9-OXO-19-NORCYCLOPROPA[G]TAX-11-ENE

This application claims the benefit of U.S. Provisional Application No. 60/482,598, filed Jun. 26, 2003 and benefit of priority of French Patent Application No. 03/04,613, filed Apr. 14, 2003.

The present invention relates to a novel process for the preparation of taxoids of general formula:

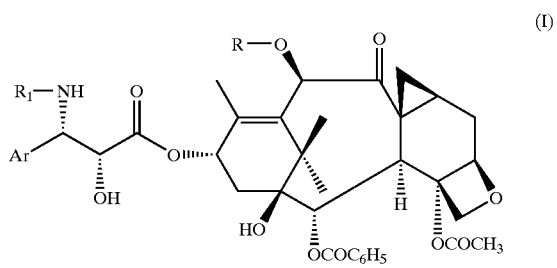

(I)

In the general formula (I),

Ar represents an aryl radical,

R represents a hydrogen atom or an acetyl, $(C_3-C_6)$ alkoxyacetyl or $(C_1-C_4)$ alkyl radical, $R_1$ represents a benzoyl radical or an $R_2$—O—CO— radical in which $R_2$ represents a straight or branched alkyl radical comprising 1 to 8 carbon atoms.

Preferably, Ar represents a phenyl radical optionally substituted by one or more atoms or radicals chosen from halogen atoms (fluorine, chlorine, bromine or iodine) and alkyl, alkoxy, alkylthio, cyano, nitro and trifluoromethyl radicals, it being understood that the alkyl radicals and the alkyl portions of the radicals comprise 1 to 4 carbon atoms, or else Ar represents an aromatic heterocyclic radical having 5 ring members and comprising one or more identical or different atoms chosen from nitrogen, oxygen or sulfur atoms.

More particularly, Ar represents a phenyl, 2- or 3-thienyl or 2- or 3-furyl radical.

More particularly still, Ar represents a phenyl radical optionally substituted by a chlorine or fluorine atom or by an alkyl (methyl), alkoxy (methoxy) or 2- or 3-thienyl or 2- or 3-furyl radical.

Of even more particular advantage is the product of general formula (I) in which Ar represents a phenyl radical, $R_1$ represents a tert-butoxycarbonyl radical and R represents an acetyl radical.

Mention may be made, among the processes known to date for preparing the compounds of formula (I), of patent EP 0 673 372, which discloses, starting from 10-deacetylbaccatin III, a process which consists, in a first stage, in protecting the 10-deacetylbaccatin III in the 7 position, in a second stage, in acetylating in the 10 position, in a third stage, in deprotecting the 7 position, in a fourth stage, in carrying out a trifluoromethanesulfonylation (or triflation) in the 7 position, in a fifth stage, in carrying out a cyclopropylation in the 7–8 position, then, in a penultimate stage, in attaching the side chain in the 13 position and, finally, in a final stage, in deprotecting the side chain. The stage of cyclopropylation in the 7–8 position is carried out in the presence either of an alkali metal halide (sodium iodide, potassium fluoride) or of an alkali metal azide (sodium azide) or of a quaternary ammonium salt or, finally, of an alkali metal phosphate.

It became apparent later, as disclosed in the patents published under the numbers WO 95/33736, WO 95/33737 and WO 96/32387, that the presence of alkali metal azide or halide (sodium iodide, potassium fluoride) was not essential and that an additive such as as molecular sieves in the presence of sodium chloride was effective. The solvent used in these three patent applications was composed of a mixture of acetonitrile and of tetrahydrofuran.

It is also known, from the paper by Johnson, Nidy, Dobrowolski, Gebhard, Qualls, Wicnienski and Kelly which appeared in Tetrahedron Letters, Vol. 35, No. 43, pp 7893–7896, 1994, that the 7-O-triflate could be converted to 7β,8β-methanotaxane in the presence of a large excess of silica gel; the excess is 60 times the weight of the 7-O-triflate derivative, which is unusable industrially.

According to the present invention, the process disclosed in the three above mentioned patents has been improved by the use of sulfolane.

The 7β,8β-methanotaxane of general formula (III)

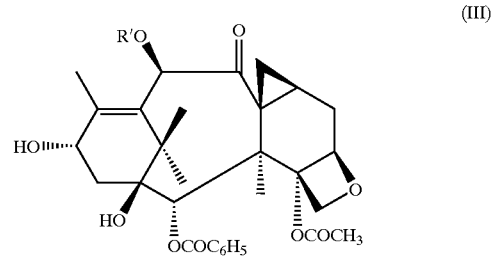

(III)

in which R' has the same meaning as R in the general formula (I) or can represent a protective group for the hydroxyl functional group when R=H in the formula (I), is obtained by the action of molecular sieve on a baccatin III or 10-deacetylbaccatin III derivative of general formula:

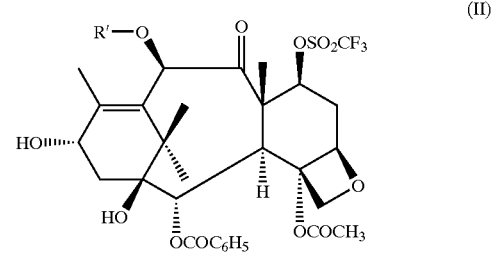

(II)

in which R' is defined as above, the reaction taking place in sulfolane.

The product of general formula (I) will subsequently be obtained by coupling a precursor of the side chain to the derivative of formula (III) according to processes known to a person skilled in the art.

In an entirely preferred way, the cyclopropylation reaction is carried out in sulfolane comprising between 2 and 5% by weight of water. The presence of water makes possible the conversion of the derivative of formula (IV) below, a by-product produced during the cyclopropanation, to the derivative of formula (V); the separation of the derivative of formulae (III) and of the derivative of formula (IV) is difficult, whereas the separation of the derivative of formula (V) from the derivative of formula (III) is easier.

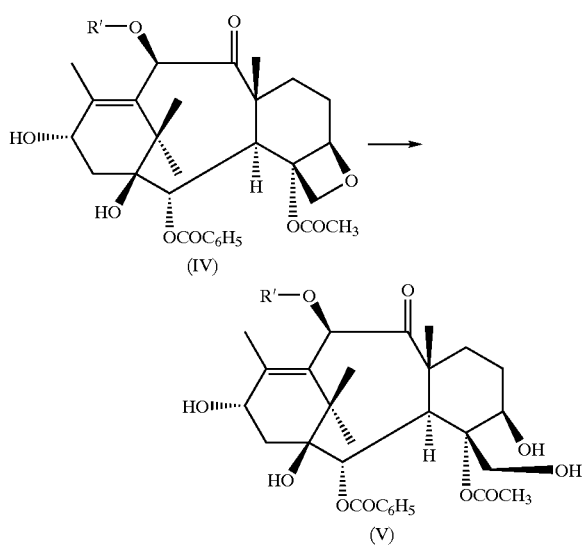

For better implementation of the invention, it is preferable to operate with an amount of water of approximately 4% by weight with respect to the sulfolane. The reaction temperature is in particular between 20° C. and the boiling point of the reaction mixture.

The addition is carried out of preferably 25 to 100% by weight of molecular sieve with respect to the substrate. As regards the reaction conditions, the reaction is generally carried out between 20° C. and the boiling point of the solvent for one to several hours.

According to a better process for implementing the invention, use will be made of the hydrated sulfolane (approximately 4% of water by weight) as reaction solvent in the presence of 100% by weight of 4 Å molecular sieves as activated powder with respect to the substrate. In this case, the reaction will be carried out at a temperature in the region of 60° C. until the substrate has been completely converted.

The product of formula (II) in which R' represents a protective group for the hydroxyl functional group or an acetyl, alkoxyacetyl or alkyl radical can be obtained by reaction of a derivative of trifluoromethanesulfonic acid, such as the anhydride or the chloride, with baccatin III or 10-deacetylbaccatin III protected on its 10 position by a protective group, such as in particular trichloroethoxycarbonyl.

Generally, the reaction of a derivative of trifluoromethanesulfonic acid is carried out in an inert organic solvent (aliphatic hydrocarbons, optionally halogenated, or aromatic hydrocarbons) in the presence of an organic base, such as a tertiary aliphatic amine (triethylamine) or pyridine, at a temperature of between −50 and +20° C.

According to a better process for implementing the invention, where one of the preferred compounds of formula (III) where R represents an acetyl group is prepared from the compound of formula (II) where R has the same meaning, after reaction of the compound of formula (II) with the molecular sieve:

the crude product is isolated by a series of treatments, such as the optional addition of a solvent, such as ethyl acetate, the removal of the insoluble materials by filtration, the concentration of the reaction medium and then the crystallization by addition of solvents which induce insolubility, such as those chosen in particular from water or toluene, then either the crude product is purified by recrystallization from a solvent or solvent mixture, such as methanol, methanol as a mixture with diisopropyl ether or toluene, sulfolane as a mixture with toluene, or methylene chloride as a mixture with diisopropyl ether, or ethyl acetate as a mixture with diisopropyl ether, or the crude product is purified by chromatography on silica gel, elution being carried out with methylene chloride as a mixture with ethyl acetate, methanol or acetonitrile.

Preferably, the medium will be treated by addition of ethyl acetate, filtration of the molecular sieve, concentration under reduced pressure and precipitation by addition of water with seeding.

Preferably, the crude product will be purified by crystallization from an ethyl acetate/diisopropyl ether mixture with a ratio of between 50/50 v/v and 10/90 v/v.

The product of formula (III) obtained is subsequently or previously coupled according to methods known to a person skilled in the art with a precursor of the side chain chosen from β-phenylisoserine protected in the 2' position, such as disclosed in patent EP 366 840, oxazolidines, such as disclosed in particular in patents EP 595 370, EP 663 906, EP 663 907, EP 663 908, EP 666 857 and EP 669 915, or β-lactams, such as disclosed in particular in the following patents EP 400 971, U.S. Pat. Nos. 5,254,580 and 5,466,834.

All of the references described herein are incorporated herein by reference in their entirety.

The following examples illustrate the present invention but should not be regarded as a limitation on the invention.

EXAMPLE 1

4,10β-Diacetoxy-2α-benzoyloxy-5β,20-epoxy-1,13α-dihydroxy-9-oxo-7β-(trifluoromethylsulfonyloxy) tax-11-ene (2.0 g) with a purity of 92%, 2.02 g of 4 Å molecular sieves as activated powder and 1.0 g of sodium chloride are charged to 14 ml of sulfolane in a 50 ml three-neck flask and the mixture is heated at 60° C. for approximately 4 hours. The reaction medium is cooled to ambient temperature and then filtered. The insoluble materials are washed in 3 times with 50 ml of ethyl acetate and the organic phases are combined. The 4,10β-diacetoxy-2α-benzoyloxy-5β,20-epoxy-1,13α-dihydroxy-9-oxo-19-norcyclopropa[g]tax-11-ene (I) thus obtained is quantitatively determined by HPLC with respect to a standard (1.29 g, yield of 88%).

Comparative Examples With Different Solvents

The results are shown in the following table:

| Example | Solvent | Conditions | DC | Yield | Observations |
| --- | --- | --- | --- | --- | --- |
| C1 | AcCN/THF 10v/1v | 15 g, reflux 3 hours | >99% | 69% | 13.5% acetamido 7.7% ethylene-1 |
| C2 | DMF | 0.5 g 40–50° C. 7 hours 30 | 98% | 70% | 16.5% ethylen-2 |
| C3 | NMP | 0.5 g 50° C., 3 hours | >99% | 12.6% | Decomposition |
| C4 | Acetone | 3 g reflux 2 hours | >99% | — | 5.6% ethylen-1 40% 7-epi OH |

-continued

| Example | Solvent | Conditions | DC | Yield | Observations |
| --- | --- | --- | --- | --- | --- |

ACETAMIDO

ETHYLEN-1 or (V)

ETHYLEN-2 or (IV)

7-epi OH

EXAMPLE 2

4,10β-Diacetoxy-2α-benzoyloxy-β,20-epoxy-1,13α-dihydroxy-9-oxo-7β-(trifluoromethylsulfonyloxy) tax-11-ene (60.0 g) with a purity of 89.8% by weight, 60 g of 4 Angstrom molecular sieves as activated powder and 9.6 ml of water are charged to 240 g of sulfolane in a 500 ml three-neck flask and the mixture is heated with stirring at 60° C. for approximately 4 hours. The reaction medium is cooled to 40° C. and 200 ml of ethyl acetate are added. The suspension is filtered through a bed of Dicalite and the insoluble material is washed 4 times with 50 ml of ethyl acetate. The organic phases are combined and the 4,10β-diacetoxy-2α-benzoyloxy-5β,20-epoxy-1,13α-dihydroxy-9-oxo-19-norcyclopropa[g] tax-11-ene thus obtained is quantitatively determined by HPLC with respect to a standard (37.5 g, yield of 88%). A fraction of the solution (152 g) is concentrated under a pressure of less than 15 mm Hg at 45° C. for approximately 45 minutes and the concentrate obtained (75.2 g) is stirred at 40° C. 59.2 ml of demineralized water are added over one hour to the solution and then seeding is carried out at 40° C. with 100 mg of 4,10β-diacetoxy-2α-benzoyloxy-5β,20-epoxy-1,13α-dihydroxy-9-oxo-19-norcyclopropa[g]tax-11-ene. The medium is cooled to ambient temperature over 2 hours 30 minutes and then 80.3 g of demineralized water are again run in over 1 hour. The suspension is then cooled to 0–4° C. over approximately 1 hour 30 minutes. The product is filtered off, washed 3 times with 33 ml of demineralized water and dried under reduced pressure at 45° C. for 16 hours. 12.65 g of crude product are thus obtained, which product has a purity of 70.8% by weight quantitatively determined by HPLC (yield of 83%).

12.5 g of crude product are charged to a 100 ml round-bottom flask and are dissolved in 25 ml of methanol at 55° C. The reaction medium is cooled to 35° C. and then seeded with a few mg of 4,10β-diacetoxy-2α-benzoyloxy-5β,20-epoxy-1,13α-dihydroxy-9-oxo-19-norcylcopropa[g] tax-11-ene. The suspension is then cooled to ambient temperature and then to 0–4° C. over approximately 3 hours. After filtration, the product is washed twice with 5 ml of diisopropyl ether and then dried under reduced pressure at 45° C. for 16 hours. 7.1 g of pure product are thus obtained, which product has a purity of 97.7% by weight quantitatively determined by HPLC (recrystallization yield of 66%).

EXAMPLES 3 to 5

Example 2 is repeated as far as the crude product, a variable amount of water being added to the sulfolane.

| Example | Conditions | ETHYLEN-1 | ETHYLEN-2 |
| --- | --- | --- | --- |
| 3 | Sieve 60° C., 4 hours | 3.6 | 5.5 |
| 4 | Sieve 60° C., 4 hours, 1% water | 6.9 | 2.4 |
| 5 | Sieve 60° C., 4 hours, 2% water | 7.9 | 1.4 |
| 2 | Sieve 60° C., 4 hours, 4% water | 8.7 | 0.2 |

The impurity named ETHYLEN-2 is difficult to separate from (III) by silica gel chromatography or crystallization; in contrast, the impurity named ETHYLEN-1 is easily removed by these same techniques.

EXAMPLE 6

Purification by Crystallization From Methanol 4,10β-Diacetoxy-2α-benzoyloxy-β,20-epoxy-1,13α-dihydroxy-9-oxo-7β-(trifluoromethylsulfonyloxy)tax-11-ene (58 g) with a purity of 92%, 58 g of 4 angstrom molecular sieves as activated powder and 29 g of sodium chloride are charged to 580 ml of ethyl acetate in a 2-liter glass reactor and the mixture is heated with stirring at between 55 and 65° C. for approximately 46 hours. The reaction medium is cooled to ambient temperature and filtered through a bed of Clarcel and the insoluble material is washed twice with 116 ml of ethyl acetate. The organic phases are combined and the 4,10β-diacetoxy-2α- benzoyloxy-5β,20-epoxy-1,13α-dihydroxy-9-oxo-19-norcyclopropa[g]tax-11-ene solution thus obtained is washed with an aqueous sodium hydrogencarbonate solution (17.4 g in 290 ml of water) and then twice with 290 ml of water. The reaction medium is concentrated to a volume of approximately 200 ml under reduced pressure at a temperature of less than 40° C. and 825 ml of methanol are added. The change in solvent is carried out by distillation under reduced pressure at a temperature of less than 40° C. with addition of methanol (1145 ml in total) and then the solution is cooled to ambient temperature. Crystallization is initiated with 0.21 g of 4,10β-diacetoxy-2α-benzoyloxy-5β,20-epoxy-1,13α-dihydroxy-9-oxo-19-norcyclopropa[g]tax-11-ene and then the suspension is cooled to 0° C. over approximately 1 hour and 30 minutes. The suspension is filtered and the product is washed twice with 116 ml of diisopropyl ether. After drying at ambient temperature to constant weight, 25 g of product are obtained (yield of 55%), which product assays at 94% by weight by HPLC quantitative determination (>99% by area internal normalization).

EXAMPLE 7

Purification by Chromatography

The crude 4,10β-diacetoxy-2α-benzoyloxy-5β,20-epoxy-1,13α-dihydroxy-9-oxo-19-norcyclopropa[g]tax-11-ene (4.9 g) with an HPLC purity of 93.9% (internal normalization of the areas) and assaying at 65.5% by weight are purified by chromatography with 250 g of silica gel, elution being carried out with a mixture of methylene chloride and ethyl acetate (v/v: 75/25). The fractions comprising the product are combined and concentrated under reduced pressure. The solution obtained (241 g) assays at 1.3% w/w by HPLC quantitative determination. The purity by HPLC is 99.4% (purification yield of 97%).

EXAMPLE 8

Purification by Crystallization From Diisopropyl Ether (DIPE)

The crude 4,10β-diacetoxy-2α-benzoyloxy-5β,20-epoxy-1,13α-dihydroxy-9-oxo-19-norcylcopropa[g]tax-11-ene (23 g) with a purity of 91% by HPLC and assaying at 77.5% by weight are dissolved in approximately 640 ml of ethyl acetate and the organic phase obtained is washed twice with 255 ml of water. The solution is then concentrated under reduced pressure at approximately 30° C. to a residual volume of approximately 74 ml. 222 ml of diisopropyl ether are then added to the solution over 4 to 7 hours at ambient temperature and then the suspension obtained is cooled to 2° C. The suspension is cooled and the product cake is washed with 36 ml of diisopropyl ether. After drying under reduced pressure at 25° C., 17.6 g of purified 4,10β-diacetoxy-2α-benzoyloxy-5β,20-epoxy-1,13α-dihydroxy-9-oxo-19-norcyclopropa[g]tax-11-ene are obtained, which product has a purity of approximately 97% and assays at 89.3% by weight (yield of 88%).

Example 8 is repeated in the following Examples 9–12 with different recrystallization solvents. The results obtained in these Examples 9–12 are tabulated below.

| Example | Conditions | RY % | ETHYLEN-1 % | ETHYLEN-2 % |
|---------|------------|------|-------------|-------------|
| 9 | AcOEt/DIPE 27/75 | 88 | 0.3 | — |
| 10 | MeOH/DIPE 70/30 | 82 | 1.7 | 0.2 |
| 11 | MeOH/toluene 50/50 | 47 | 0.3 | 0.2 |
| 12 | AcOEt/DIPE 50/50 | 88 | 0.2 | — |

What is claimed is:
1. A process for the preparation of a compound of formula (I)

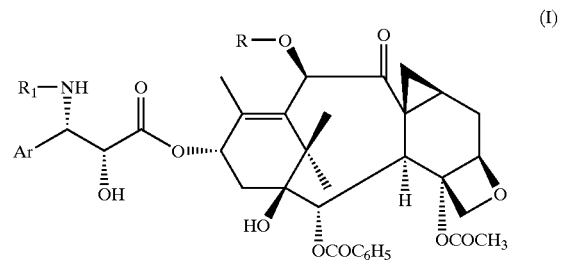

wherein:

Ar is aryl;

R is hydrogen, acetyl, alkoxyacetyl or alkyl;

$R_1$ is benzoyl or $R_2$—O—CO— wherein $R_2$ is straight or branched $C_1$–$C_8$ alkyl;

comprising contacting compound of formula (II) with a weak base, then successively or beforehand, coupling a precursor of the side chain and, deprotecting the optionally protected hydroxyl functional group, which comprises carrying out the cyclopropanation reaction in sulfolane;

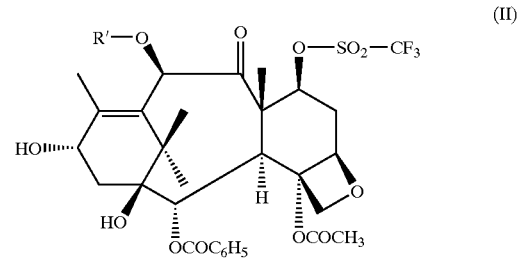

wherein R' is a protective group for the hydroxyl functional group or acetyl, alkoxyacetyl or alkyl.

2. The process as set forth in claim 1, wherein R is acetyl, $R_1$ is tert-butoxycarbonyl and Ar is phenyl.

3. The process as set forth in claim 1, wherein the weak base is a molecular sieve having a pore size of 4 Å.

4. The process as set forth in claim 1, wherein the reaction is carried out in the presence of 4 Å molecular sieve as activated powder.

5. The process as set forth in claim 3, wherein the molecular sieve and the compound of formula (II) are present in about 1:1 ratio by weight.

6. The process as set forth in claim 4, wherein the molecular sieve and the compound of formula (II) are present in about 1:1 ratio by weight.

7. The process as set forth in claim 1, wherein the sulfolane contains from about 2 to about 5% by weight of water.

8. The process as set forth in claim 7, wherein the sulfolane contains about 4% of water.

9. The process as set forth in claim 1, wherein the reaction is carried out at a temperature of from about 20° C. to about the boiling point of the solvent.

10. The process as set forth in claim 9, wherein the reaction temperature is about 60° C.

11. The process as set forth in claim 3, wherein the compound of formula (I) is isolated as a crude product by addition of ethyl acetate to the reaction medium, filtration of the molecular sieve, concentration of the reaction medium and then crystallization by addition of water.

12. The process as set forth in claim 11, wherein the crude product is further purified by recrystallization from a solvent or solvent mixture chosen from methanol, a mixture of methanol and diisopropyl ether, a mixture of methanol and toluene, a mixture of sulfolane and toluene, a mixture of methylene chloride and diisopropyl ether, or a mixture of ethyl acetate and diisopropyl ether.

13. The process as set forth in claim 12, wherein the crude product is purified with a mixture of ethyl acetate and isopropyl ether.

14. The process as set forth in claim 13 wherein said solvent mixture is present in a ratio of approximately 25/75 v/v.

15. The process as set forth in claim 1, wherein the precursor of the side chain is chosen from β-phenylisoserine protected in the 2' position, oxazolidines or β-lactams.

16. A process for the preparation of a compound of formula (III):

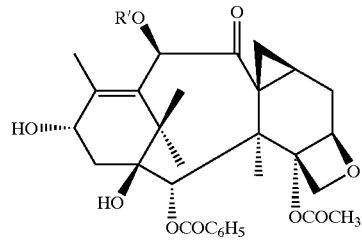

wherein R' is a protective group for the hydroxyl functional group or acetyl, alkoxyacetyl or alkyl;
comprising bringing a compound of general formula (II)

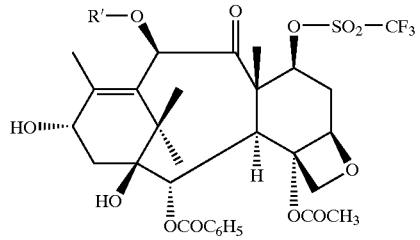

into contact with a 4 Å molecular sieve, which is carried out in sulfolane.

17. The process as set forth in claim 16, wherein the reaction is carried out in the presence of 4 Å molecular sieve as activated powder.

18. The process as set forth in claim 16, wherein the sulfolane contains from about 2 to about 5% by weight of water.

19. The process as set forth in claim 16, wherein the sulfolane contains about 4% of water.

20. The process as forth in claim 16, wherein the reaction is carried out at a temperature of from about 20° C. to about the boiling point of the solvent.

* * * * *